United States Patent
Tung et al.

(10) Patent No.: US 10,676,414 B2
(45) Date of Patent: *Jun. 9, 2020

(54) PROCESS FOR THE MANUFACTURE OF 1,1,1,3,3-PENTACHLOROPROPANE

(71) Applicant: HONEYWELL INTERNATIONAL INC.

(72) Inventors: Hsueh Sung Tung, Getzville, NY (US); Ian Shankland, Randolph, NJ (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/681,972

(22) Filed: Aug. 21, 2017

(65) Prior Publication Data

US 2018/0127337 A1 May 10, 2018

Related U.S. Application Data

(63) Continuation of application No. 11/869,274, filed on Oct. 9, 2007, now Pat. No. 9,738,577.

(60) Provisional application No. 60/850,910, filed on Oct. 11, 2006.

(51) Int. Cl.
| | | |
|---|---|---|
| *C07C 17/00* | (2006.01) | |
| *C07C 17/20* | (2006.01) | |
| *C07C 17/275* | (2006.01) | |
| *C07C 17/278* | (2006.01) | |
| *C07C 19/08* | (2006.01) | |
| *C07C 19/01* | (2006.01) | |
| *C07C 21/18* | (2006.01) | |

(52) U.S. Cl.
CPC ............ *C07C 17/00* (2013.01); *C07C 17/206* (2013.01); *C07C 17/275* (2013.01); *C07C 17/278* (2013.01); *C07C 19/01* (2013.01); *C07C 19/08* (2013.01); *C07C 21/18* (2013.01)

(58) Field of Classification Search
None
See application file for complete search history.

(56) References Cited

U.S. PATENT DOCUMENTS

| | | | | |
|---|---|---|---|---|
| 5,902,914 A | * | 5/1999 | Rygas | C07C 17/278 570/172 |
| 6,300,532 B1 | * | 10/2001 | Van Der Puy | C07C 17/275 560/226 |
| 7,102,041 B2 | * | 9/2006 | Tung | C07C 17/275 570/101 |
| 9,738,577 B2 | * | 8/2017 | Tung | C07C 17/00 |
| 2006/0122441 A1 | * | 6/2006 | Tung | C07C 17/275 570/171 |

* cited by examiner

*Primary Examiner* — Clinton A Brooks
(74) *Attorney, Agent, or Firm* — Faegre Drinker Biddle & Reath LLP

(57) ABSTRACT

A process for the manufacture of haloalkanes, or more particularly to a process for the manufacture of 1,1,1,3,3-pentachloropropane (HCC-240fa) and/or 1,1,1,3-tetrachloropropane (HCC-250fb). The process includes (a) mixing a catalyst, co-catalyst and a haloalkane starting material under conditions suitable to produce a homogeneous mixture; (b) reacting the homogeneous mixture with a haloalkene and/or alkene starting material under conditions suitable to produce a haloalkane product stream; and (c) recovering a haloalkane product from said product stream.

21 Claims, 1 Drawing Sheet

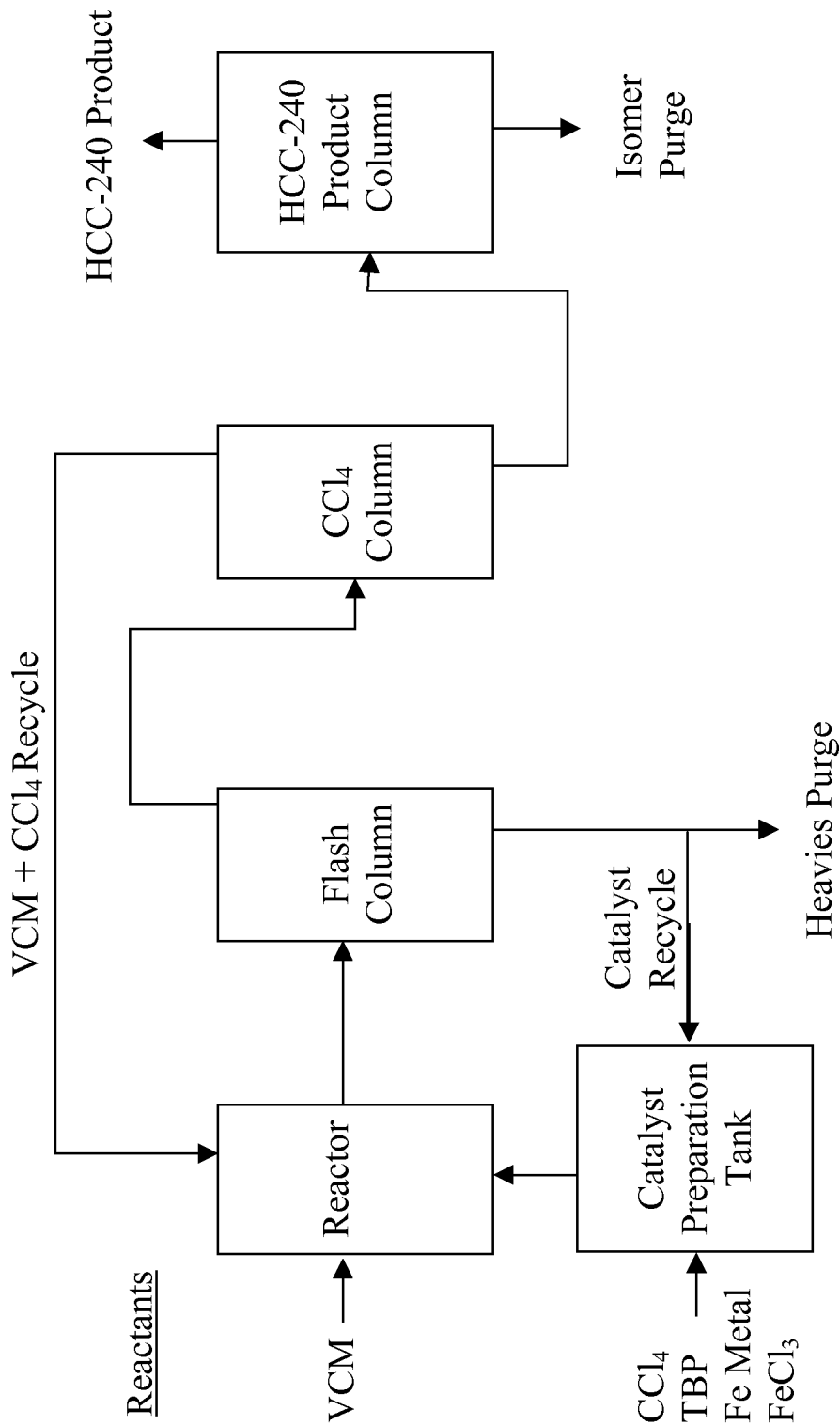

PROCESS FOR THE MANUFACTURE OF 1,1,1,3,3-PENTACHLOROPROPANE

CROSS-REFERENCE TO RELATED APPLICATION

This application is a continuation of U.S. application Ser. No. 11/869,274, filed Oct. 9, 2007, which application claims the benefit of U.S. provisional patent application 60/850,910, filed on Oct. 11, 2006, which application is incorporated herein by reference.

BACKGROUND OF THE INVENTION

The invention pertains to a process for the manufacture of haloalkanes, or more particularly to a process for the manufacture of 1,1,1,3,3-pentachloropropane (HCC-240fa) and/or 1,1,1,3-tetrachloropropane (HCC-250fb).

Addition reactions for preparing useful haloalkanes, such as 1,1,1,3,3-pentachloropropane (HCC-240fa), are known in the art. Typically, in this reaction, a halogenated compound, such as carbon tetrachloride, is added to an olefinic compound, such as vinyl chloride monomer (VCM), in the presence of a catalyst and under conditions sufficient to form a haloalkane product having a backbone longer than that of the haloalkane reactant. The halogenated product then is recovered by separating it from the reactants, catalyst and by-products using conventional techniques such as distillation.

Although widely used, this process suffers from several shortcomings, one of the more serious being that the process is not readily adapted to continuous operation. The problem is due, in large part, to the recovery of the halogenated product from the product stream. Often such recovery destroys the catalyst, thereby eliminating the ability to recycle the catalyst. For example, Kotota et al. "Addition of Tetrachloromethane to Halogenated Ethenes Catalyzed by Transition Metal Complexes", 77 *J. Molec. Catal.*, 51-60 (1992), discloses a batch process for the preparation of HCC-240fa from carbon tetrachloride and vinyl chloride using as a catalyst, cuprous salts, cuprous chloride and $Cu[(CH_3-CN)_4]ClO_4$, complexed with a co-catalyst, namely, n-butylamine. To recover the halogenated product, the catalyst and co-catalyst are removed by a water wash which destroys the catalyst. Since the catalyst is destroyed, it cannot be recycled. Reusing catalyst, however, is important to a commercially-viable, continuous process.

Other recovery processes disrupt the preparation process, thereby complicating a continuous process or frustrating it altogether. For example, in conventional processes, where recovery is effected by distilling a product stream to separate the haloalkane from the reactants and catalyst, the more volatile co-catalysts tend to flash off thus leaving a solid catalyst in the distillation column. Eventually, the process must be interrupted and the catalyst removed from the column, filtered, and physically transported to another vessel where it is mixed with the co-catalyst and introduced back to the reaction. In addition to disrupting the process, these recovery steps add cost and complexity to the reaction process.

Aside from the shortcomings related to recovering the haloalkane product, conventional addition reactions tend to have low selectivities. For example, Kotora et al., "Selective Additional of Polyhalogenated Compounds to Chlorosubstituted Ethenes Catalyzed by a Copper Complex," *React. Kinet. Catal. Lett.*, 415-19 (1991) discloses batch preparation of HCC-240 from carbon tetrachloride and vinyl chloride using a cuprous chloride complex catalyst with 2-propylamine as a co-catalyst. The reported HCC-240 yield, however, is only 71%. Additionally, Zhiryukina et al. "Synthesis of Polychloroalkanes With Several Different Chlorine-Containing Groups," 1 *Izv. Akad. Nauk SSR*, Ser. Khim. 15257 (1983) also disclose a batch process for preparing HCC-240 from carbon tetrachloride and vinyl chloride using a $Fe(CO)_5$-ethanol catalyst, which process reportedly yields 25% HCC-240. All of the above-disclosed processes are disadvantageous in that they are batch processes of low productivity and they have low selectivity for HCC-240. The Zhiryukina et al. process is further disadvantageous because it uses a highly toxic catalyst.

Therefore, a need exists for an efficient and economical continuous process for producing haloalkanes such as HCC-240fa in high yield. Further, HCC-240fa is a commercial raw material for the manufacture of HFC-245fa, and a need exists to develop alternative technologies to manufacture this material. The present invention addresses these needs, among others. Particularly, the present invention relates to new catalyst and co-catalyst systems, and to a new concept of dissolving a catalyst and co-catalyst in one of the reactants, e.g. $CCl_4$, to form a homogeneous mixture. Subsequently, this mixture is fed to a reaction zone along with another reactant, e.g. VCM, preferably in a solid-free reaction.

BRIEF DESCRIPTION OF THE DRAWINGS

FIG. 1 is a flow chart illustrating a process of the invention for producing HCC-240fa.

DETAILED DESCRIPTION OF THE INVENTION

The invention provides a process for preparing a haloalkane comprising:
(a) mixing a catalyst, co-catalyst and a haloalkane starting material under conditions suitable to produce a homogeneous mixture;
(b) reacting the homogeneous mixture with a haloalkene starting material, an alkene starting material or both a haloalkene starting material and an alkene starting material under conditions suitable to produce a haloalkane product stream; and
(c) recovering a haloalkane product from said product stream.

The invention also provides a process for preparing a haloalkane, comprising the steps of:
(a) mixing a catalyst, co-catalyst and a haloalkane starting material under conditions suitable to produce a homogeneous mixture;
(b) reacting the homogeneous mixture with a haloalkene starting material, an alkene starting material or both a haloalkene starting material and an alkene starting material under conditions suitable to produce a haloalkane product stream;
(c) flash-distilling the haloalkane product stream of step (b) to separate a haloalkane product, unreacted haloalkane starting material and unreacted haloalkene starting material from a mixture of said catalyst and co-catalyst; and (d) recycling the catalyst and co-catalyst mixture to step (a).

The invention further provides a process for preparing 1,1,1,3,3-pentafluoropropane and/or a combination of 1,1,1,3-tetrachloropropane and 3,3,3-trifluoro-1-propene comprising:

(a) mixing a catalyst, co-catalyst and a haloalkane starting material under conditions suitable to produce a homogeneous mixture;
(b) reacting the mixture with a haloalkene starting material and/or alkene starting material under conditions suitable to produce a 1,1,1,3,3-pentachloropropane and/or 1,1,1,3-tetrachloropropane product stream;
(c) recovering 1,1,1,3,3-pentachloropropane and/or 1,1,1,3-tetrachloropropane from said product stream; and
(d) reacting said 1,1,1,3,3-pentachloropropane and/or 1,1,1,3-tetrachloropropane with hydrogen fluoride under conditions sufficient to yield 1,1,1,3,3-pentafluoropropane and/or a combination of 1,1,1,3-tetrafluoropropane and 3,3,3-trifluoro-1-propene.

The present invention provides a highly selective process for the production of halogenated alkanes in good yield in which process unreacted materials may be recycled. More specifically, the invention provides a process for producing 1,1,1,3,3-pentachloropropane (HCC-240fa) and/or 1,1,1,3-tetrachloropropane (HCC-2501b). HCC-240fa may be used as a raw material for the production of 1,1,1,3,3-pentafluoropropane ("HFC-245 fa"), 1,1,1,3-tetrafluoropropane and 3,3,3-trifluoro-1-propene.

The process may be conducted with or without a solvent, wherein a catalyst and co-catalyst are dissolved in a haloalkane reactant to form a homogenous mixture, followed by feeding the mixture to a reaction zone along with a haloalkene reactant. The reaction is most preferably a solid-free reaction. This may be accomplished simply due to the nature of the reactants and/or catalysts or by removal of solids such as by filtration or by decantation. After reaction, the reactor effluent is distilled, preferably flash-distilled, to separate a haloalkane reaction product (e.g. HCC-240fa or HCC-2501b), any unreacted haloalkane starting material (e.g. $CCl_4$) and any unreacted haloalkene or alkene starting material (e.g. VCM or ethylene) from a catalyst/co-catalyst mixture. The catalyst/co-catalyst mixture is then preferably recycled back to a catalyst preparation tank as a mixture. The process may be carried out in either a batch or a continuous system. The production system may also be closed to provide substantially complete recycling of any unreacted haloalkane starting material and haloalkene starting material or alkene starting material.

In the first step (a) of the process of the present invention, a catalyst and a co-catalyst are mixed with a haloalkane starting material under conditions suitable to produce a mixture. The catalysts useful in the present invention include metal ions and neutral metallic species. Suitable catalysts include cuprous salts, organometallic cuprous compounds, iron wire, iron shavings, iron powder, and iron chlorides. Exemplary cuprous salts and organometallic cuprous compounds include, without limitation, cuprous chloride (CuCl), cuprous bromide, cuprous cyanide, cuprous sulfate, and cuprous phenyl. The iron powder useful in this invention is preferably a fine powder of pure metallic iron, preferably with a particle size smaller than 325 mesh. Preferably, cuprous chloride or iron powder is used as the catalyst.

Co-catalysts useful in the present invention are organic ligands capable of forming a complex with the catalyst used and capable of bringing the catalyst into solution. Suitable ligands include organic amines, such as, without limitation, tert-butylamine, n-butylamine, sec-butylamine, 2-propylamine, benzylamine, tri-n-butylamine, pyridine and combinations thereof. The preferred organic amine is tert-butylamine. Alternatively, the co-catalyst may be a nitrile including, without limitation, acetonitrile, propionitrile, n-butyronitrile, benzonitrile, phenylacetonitrile and combinations thereof. The preferred nitrile is acetonitrile. As another alternative, the co-catalyst may be an amide including, without limitation, hexamethylphosphoramide (HMPA), dimethylformamide and combinations thereof. Hexamethylphosphoramide is the most preferred amide. Also suitable are combinations of amines, nitriles, amides, phosphate and phosphates. The co-catalysts are chelating agents and may also serve as solvents. A solvent may help dissolve the solid catalyst. When a solvent is used, it preferably serves as the co-catalyst. Useful solvents non-exclusively include nitrile compounds. The catalysts, co-catalysts and solvents useful in the present invention are commercially available.

The catalysts and co-catalysts useful in the present invention form a catalyst-co-catalyst system. In a preferred catalyst-co-catalyst system, the catalyst is CuCl and the co-catalyst is acetonitrile ($CH_3CN$), tert-butylamine (t-Bu-$NH_2$), n-butylamine (n-Bu-$NH_2$), sec-butylamine (sec-Bu-$NH_2$), benzyl-amine (benzyl-$NH_2$), ethanol-amine, pyridine or tri-n-butylamine (n-$Bu_3$N). In another preferred catalyst-co-catalyst system, the catalyst is iron powder, or iron wire, and/or ferric chloride and the co-catalyst is HMPA, tributylphosphite ($(BuO)_3P$), trichloroethylphosphite ($(ClCH_2CH_2O)_3P$), triphenylphosphite ($(PhO)_3P$), tributylphosphate, or triphenylphosphate. More preferably, the catalyst-co-catalyst system is cuprous chloride/tert-butylamine, cuprous chloride/acetonitrile, iron powder/hexamethylphosphoramide or iron powder/tributylphosphate. Most preferably, cuprous chloride/tert-butylamine or iron powder/tributylphosphate is used.

Haloalkanes useful in the process of the present invention are of the formula $C_nH_mX_p$ wherein n is an integer from 1 to 200, preferably from 1 to 20, most preferably from 1 to 4, X is a halogen such as fluorine, chlorine, bromine, iodine, or mixtures thereof, and m and p are each independently 0 to 2n+2 provided that m+p=2n+2. Exemplary haloalkanes include, without limitation, carbon tetrachloride ($CCl_4$), 1,1,1-trichloroethane, dichlorofluoromethane, 1,1,1-trichlorotrifluoroethane, 1,1,2-trichlorotrifluoroethane, tetrachloroethane, pentachloroethane, and hexachloroethane. Such useful haloalkane starting materials are commercially available.

Haloalkenes and alkenes useful in the process of the present invention are of the formula $C,HyX_z$ wherein n is an integer from 2 to 200, preferably from 2 to 20 and most preferably from 2 to 4, X is a halogen such as fluorine, chlorine, bromine, iodine, or mixtures thereof, and y and z are each independently 0 to 2n provided that y+z=2n. Exemplary haloalkenes and alkenes include, without limitation, ethylene, propylene, butylene, vinyl chloride, 1,1-dichloroethene, trichloroethene, tetrachloroethene, chlorofluoroethene, 1,2-dichloroethene, 1,1-dichlorodifluoroethene, 1-chloro-1-propene, 2-chloro-1-propene, 1-chloro-1-butene and 2-chloro-1-butene. Such useful haloalkene and alkene starting materials are also commercially available.

The specific haloalkane and haloalkene/alkene used, as well as the catalyst, co-catalyst, and reaction conditions used will depend on the desired product. For example, for the production of HCC-240fa, the preferred haloalkane feed material is carbon tetrachloride, available from Occidental Chemical Corp. of Dallas, Tex. and the preferred haloalkene is vinyl chloride, available from PPG Industries, Pittsburgh, Pa. For the production of 1,1,1,3-pentachlorobutane, the preferred haloalkene feed material is 2-chloro-1-propene.

The catalyst and co-catalyst are used in amounts sufficient to catalyze the reaction of the haloalkane starting material and haloalkene starting material. Generally, the amount used is a mole ratio of catalyst to co-catalyst from about 0.01:1 to about 500:1, preferably from about 1:1 to about 100:1. The mole ratio of copper to t-butylamine is about 0.05:1 to about 20:1, preferably about 0.02:1 to 1.0:1, and more preferably about 0.1:1 to about 0.7:1. The mole ratio of iron powder to tributylphosphate may be about 0.05:1 to about 500.0:1, preferably about 1.0:1 to about 100.0:1, and more preferably about 1.5:1 to about 10:1. The preferred concentration of the catalyst in the reaction mixture is from about 0.001 to about 20 weight percent, preferably from about 0.01 to about 10 weight percent, and more preferably from about 0.1 to about 5 weight percent. Generally, the mole ratio of haloalkane to haloalkene is from about 0.02:1 to about 50:1. Preferably, the ratio is from about 0.1:1 to about 4.0:1 and more preferably from about 1:1 to about 3:1 haloalkane to haloalkene or alkene.

In the inventive process, the catalyst, co-catalyst and a haloalkane starting material are mixed to produce a mixture. To form this mixture, the catalyst may be added to a mixing tank (catalyst preparation tank) containing the haloalkane starting material and/or co-catalyst. Alternatively, the co-catalyst may be added to a mixing tank containing the catalyst and haloalkane. Most preferably, the catalyst and co-catalyst are mixed first in the mixing tank followed by adding the haloalkane to form said mixture. During this step, the temperature of the mixing tank may be higher than or lower than the temperature of the reactor, but preferably is maintained at the same temperature as that of the reactor. Thereafter, the catalyst/co-catalyst/haloalkane mixture is filtered by using a filtration device internal or external to the mixing tank to form a homogenous mixture. The resulting homogeneous mixture is fed along with the haloalkene or alkene into a reactor at the desired reaction temperature, thereby reacting the mixture with the haloalkene or alkene starting material under conditions suitable to produce a haloalkane product stream. The process may be conducted with or without a solvent. Useful solvents include $CH_3CN$ (which is also a co-catalyst) and other nitriles. In the absence of a solvent, it is preferred to use a large excess of the haloalkane reactant, such as $CCl_4$ for the formation of HCC-240fa.

The reactor is heated to a temperature of from about 40° C. to about 180° C., preferably from about 85° C. to about 150° C., with agitation and under the vapor pressure of the reagents. The reaction is preferably carried out until a conversion or haloalkene or alkene higher than 95% is achieved, generally for a residence time of from about 0.01 hours to about 24 hours, preferably from about 1 hour to about 12 hours. In the next step of the process, the haloalkane product stream is flash-distilled to remove a "top" stream including unreacted haloalkane (e.g. $CCl_4$) and haloalkene or alkene (e.g. VCM or ethylene) feed materials and the haloalkane reaction product (e.g. HCC-240fa or HCC-2501b), while the catalyst/co-catalyst mixture remains. The distillation may be performed in one or more distillation columns, which are well known in the art. Preferably, the flash-distillation is conducted in two steps: first, flash-distillation is conducted at a temperature less than the reaction temperature under a pressure, preferably under vacuum, to remove the haloalkane reaction product, followed by another vacuum flash-distillation at a lower pressure to remove any unreacted haloalkane and/or haloalkene or alkene. The "bottoms" stream is fed back to the mixing tank and recycled back to the reactor. The distilled, unreacted haloalkane and haloalkene or alkene may be recycled back to the reactor.

In a later step of the process of the present invention provides for the purification of the crude product by distillation. Fractional vacuum distillation is carried out at about 5 to about 200 mm Hg and a temperature of about 50° C. to about 150° C. to recover the product. It has been discovered that when this purification step is carried out in the presence of a trialkyl phosphate such as tributyl phosphate or other metal chelating compound, the distillation yield of purified product is significantly improved. Although not seeking to be bound by any particular theory, it is believed that the tributylphosphate acts to prevent the decomposition of the product haloalkane. Thus, in a preferred embodiment, the purification step includes the addition of an amount of a metal chelating compound sufficient to improve the haloalkane product yield. Preferably, 5 weight percent of tributyl phosphate is used.

In a preferred embodiment of the invention, the above process is conducted to prepare 1,1,1,3,3-pentafluoropropane (HFC-245fa), wherein (a) the catalyst, co-catalyst and a haloalkane starting material are combined under conditions suitable to produce a homogeneous mixture; (b) the mixture is reacted with a haloalkene starting material under conditions suitable to produce a 1,1,1,3,3-pentachloropropane product stream; (c) the 1,1,1,3,3-pentachloropropane is then recovered from said product stream; and (d) said 1,1,1,3,3-pentachloropropane is then reacted with hydrogen fluoride under conditions sufficient to yield 1,1,1,3,3-pentafluoropropane. In this embodiment, the haloalkane starting material preferably comprises carbon tetrachloride, the haloalkene starting material preferably comprises vinyl chloride, and the catalyst/co-catalyst system preferably comprises either cuprous chloride/tert-butylamine or iron powder/tributylphosphate.

In another preferred embodiment of the invention, the above process is conducted to prepare a combination of 1,1,1,3-tetrafluoropropane and 3,3,3-trifluoro-1-propene, wherein (a) the catalyst, co-catalyst and a haloalkane starting material are combined under conditions suitable to produce a homogeneous mixture; (b) the mixture is reacted with an alkene starting material under conditions suitable to produce a 1,1,1,3-tetrachloropropane product stream; (c) the 1,1,1,3-tetrachloropropane is then recovered from said product stream; and (d) said 1,1,1,3-tetrachloropropane is then reacted with hydrogen fluoride under conditions sufficient to yield a combination of 1,1,1,3-tetrafluoropropane and 3,3,3-trifluoro-1-propene. In this embodiment, the haloalkane starting material preferably comprises carbon tetrachloride, the alkene starting material preferably comprises ethylene, and the catalyst/co-catalyst system preferably comprises either cuprous chloride/tert-butylamine or iron powder/tributylphosphate. The above reaction will lead to the production of both 1,1,1,3-tetrafluoropropane and 3,3,3-trifluoro-1-propene in varying yields depending on the reaction conditions with hydrogen fluoride. When the hydrogen fluoride is reacted in the liquid phase, 1,1,1,3-tetrafluoropropane product yield will be greater than 3,3,3-trifluoro-1-propene product yield. When the hydrogen fluoride is reacted in the vapor phase, 1,1,1,3-tetrafluoropropane product yield will be less than 3,3,3-trifluoro-1-propene product yield.

Further, a plurality of reactions including one or more haloalkene starting materials and one or more alkene starting materials may also be conducted together in the same reaction vessel to form a plurality of reaction products. For example, a homogeneous mixture of a catalyst, co-catalyst and a haloalkane starting material may be reacted with both a haloalkene starting material (e.g. VCM) and an alkene starting material (e.g. ethylene) in a vessel under conditions suitable to produce one or more haloalkane products (e.g. 1,1,1,3,3-pentachloropropane produced from a haloalkene starting material and/or 1,1,1,3-tetrachloropropane, produced from an alkene starting material).

The process of the present invention and its use will be clarified further by a consideration of the following examples. In addition, the disclosures of U.S. Pat. Nos. 5,902,914 and 6,187,978 are hereby incorporated by reference.

EXAMPLE 1

In a Monel autoclave heated to 150° C., 1.8 g cuprous chloride (0.018 mol) and 230 g acetonitrile (5.6 moles) are mixed with 431 g carbon tetrachloride (2.8 moles) to form a mixture. The acetonitrile also serves as a solvent. Solid CuCl remains in the solution and is removed from the mixture by decantation. Thereafter, 98 g (1.57 moles) of vinyl chloride monomer are added to react with this mixture that contains carbon tetrachloride. The reaction time is 10 hours and the initial pressure is about 220 psig. HCC-240 is produced with 95 mol. % selectivity and VCM conversion is 95 mol. %. HCC-470 ($CCl_3CH_2CHClCH_2CHCl_2$) and HCC-240db ($CCl_3CHClCH_2Cl$) are formed as byproducts.

EXAMPLE 2

In a Monel autoclave heated to 95° C., 2.5 g cuprous chloride (0.025 mol) and 5.2 g t-butylamine (0.07 mole) are mixed with 634 g (4.1 moles) of carbon tetrachloride to form a mixture. No solvent is used. Solid CuCl remains in the solution and is removed from the mixture by decantation. Thereafter, 119 g (1.9 moles) of vinyl chloride monomer is added to react with the carbon tetrachloride mixture. The reaction time is 10 hours and the initial pressure is about 220 psig. HCC-240 is produced with 93 mol. % selectivity and VCM conversion is 66 mol. %. HCC-470 ($CCl_3CH_2CHClCH_2CHCl_2$) and HCC-240db ($CCl_3CHClCH_2Cl$) are formed as byproducts.

EXAMPLE 3

In a catalyst preparation tank, as shown in FIG. 1, about 10 kg of iron powder and 1.3 kg of $CCl_4$ are added. The tank is equipped with an agitator and is heated to 100° C. after adding the 10 kg of iron powder and 1.3 kg of $CCl_4$. Subsequently, 9.2 kg/hr of $CCl_4$, 0.24 kg/hr of tributylphosphate, and 0.29 kg/hr of ferric chloride are added and mixed in the tank. The mixed solution is passed through a filtration screen at the outlet of the tank and fed to a reactor that is controlled at 100° C. A separate feed line is used to feed 3.8 kg/hr vinyl chloride directly into the reactor. The pressure of the reactor is maintained at about 7 kg/cm². The crude product leaving the reactor is fed to a flash-distillation column. The flash-distillation column is run under a slight vacuum. The overhead of the flash column is fed to a fractionation column (see $CCl_4$ Column in FIG. 1) where un-reacted $CCl_4$ and vinyl chloride are distilled and fed back to the reactor. The bottom of the flash column that contains catalyst and co-catalyst are recycled back to the mixing tank (i.e. Catalyst Preparation Tank in FIG. 1). The bottom of the $CCl_4$ Column is fed to another fractionation column (i.e. the HCC-240 Product Column). Purified HCC-240 is isolated as distillate from the overhead stream of the HCC-240 Product Column. Heavy by-products are removed out of the system from the bottom of the Product Column and the heavy purge in the catalyst recycle line. The yields of $CCl_4$ and VCM are greater than 90%, respectively. HCC-470 ($CCl_3CH_2CHClCH_2CHCl_2$) and HCC-240db ($CCl_3CHClCH_2Cl$) are formed as byproducts.

EXAMPLE 4

The same reactor system, raw materials of $CCl_4$, catalyst, and co-catalyst are used in the same quantities as described in EXAMPLE 3, except that vinyl chloride is replaced by ethylene. The equivalent amounts of ethylene in "moles per hour" used are the same as that of vinyl chloride. The process produces 1,1,1,3-tetrachloropropane in good quality. The yield of $CCl_4$ and ethylene are both greater than 90%.

While the preferred embodiments of the present invention are particularly shown herein, it will be readily appreciated by those of ordinary skill in the art that various changes and modifications may be made without departing from the spirit and scope of the invention. It is intended that the claims be interpreted to cover the disclosed embodiments, any alternatives which are discussed herein and all equivalents thereto.

What is claimed is:

1. A process for preparing a haloalkane comprising:
    (a) preparing a solid-free mixture comprising a catalyst, carbon tetrachloride, and vinyl chloride;
    (b) reacting the solid-free mixture under conditions suitable to produce a haloalkane product stream;
    (c) recovering 1,1,1,3,3-pentachloropropane from said product stream; and
    (d) reacting said 1,1,1,3,3-pentachloropropane with hydrogen fluoride under conditions sufficient to yield 1,1,1,3,3-pentafluoropropane; and
    wherein the process is a continuous process.

2. The process of claim 1 wherein said catalyst comprises CuCl and said co-catalyst comprises $CH_3CN$, t-Bu-$NH_2$, n-Bu-$NH_2$, ethanol-amine, pyridine, sec-Bu-$NH_2$, benzyl-$NH_2$, n-$Bu_3N$ or combinations thereof.

3. The process of claim 1 wherein said catalyst comprises metallic Fe and said co-catalyst comprises hexamethylphosphoramide, $(BuO)_3P$, $(ClCH_2CH_2O)_3P$, tributylphosphate, triphenylphosphate, $(PhO)_3P$ or combinations thereof.

4. The process of claim 1 wherein said haloalkane starting material has the formula $C_nH_mX_p$ wherein X is a halogen and wherein n is an integer from 1 to 200, and m and p are each independently 0 to 2n+2 provided that m+p=2 n+2.

5. The process of claim 1 wherein said haloalkene starting material has the formula $C_nH_yX_z$ wherein X is a halogen and wherein n is an integer from 2 to 200, and y and z are each independently 0 to 2 n provided that y+z=2 n.

6. The process of claim 1 wherein the product stream comprises a portion of said catalyst and a portion of said co-catalyst, and said process further comprises recovering and recycling said catalyst and said co-catalyst from said product stream.

7. The process of claim 6 wherein said catalyst and said co-catalyst are recovered and recycled as a mixture of the catalyst and co-catalyst.

8. The process of claim 1 wherein said catalyst comprises iron and said co-catalyst comprises tributylphosphate.

9. A process for preparing a haloalkane, comprising the steps of:
    (a) preparing a solid-free mixture comprising a catalyst, co-catalyst and a haloalkane starting material;
    (b) reacting the solid-free mixture with a haloalkene starting material, an alkene starting material or both a haloalkene starting material and an alkene starting material under conditions suitable to produce a haloalkane product stream comprising 1, 1, 1, 3, 3-pentachloropropane;

(c) flash-distilling the haloalkane product stream of step (b) to separate a haloalkane product comprising 1, 1, 1, 3, 3-pentachloropropane, unreacted haloalkane starting material and unreacted haloalkene starting material from a mixture of said catalyst and co-catalyst; and (d) recycling the catalyst and co-catalyst mixture to step (a);

wherein the process is a continuous process.

10. The process of claim 9 wherein said haloalkane product comprises 1,1,1,3,3-pentachloropropane, 1,1,1,3-tetrachloropropane, 1,1,1,3,3-pentachlorobutane or a combination thereof.

11. The process of claim 9 wherein said catalyst comprises iron and said co-catalyst comprises tributlyphosphate.

12. A process for preparing 1,1,1,3,3-pentafluoropropane and/or a combination of 1,1,1,3-tetrachloropropane and 3,3,3-trifluoro-1-propene comprising:

(a) preparing a solid-free mixture comprising a catalyst, co-catalyst and a haloalkane starting material;

(b) reacting the solid-free mixture with a haloalkene starting material and/or alkene starting material under conditions suitable to produce a 1,1,1,3,3-pentachloropropane product stream;

(c) recovering 1,1,1,3,3-pentachloropropane from said product stream; and (d) reacting said 1,1,1,3,3-pentachloropropane with hydrogen fluoride under conditions sufficient to yield 1,1,1,3,3-pentafluoropropane;

wherein the process is a continuous process.

13. The process of claim 12 wherein said haloalkene starting material comprises vinyl chloride, 2-chloro-1-propene or a combination thereof.

14. The process of claim 12 wherein said alkene starting material comprises ethylene.

15. The process of claim 12 wherein said catalyst comprises CuCl and said co-catalyst comprises $CH_3CN$, t-Bu-$NH_2$, n-Bu-$NH_2$, ethanol-amine, pyridine, sec-Bu-$NH_2$, benzyl-$NH_2$, n-$Bu_3$N or combinations thereof.

16. The process of claim 12 wherein said catalyst comprises metallic Fe and said co-catalyst comprises hexamethylphosphoramide, $(BuO)_3P$, $(ClCH_2CH_2O)_3P$, tributlyphosphate, triphenylphosphate, $(Pho)_3P$ or combinations thereof.

17. The process of claim 12 wherein said haloalkane product is recovered from said product stream by flash-distillation.

18. The process of claim 12 wherein the product stream comprises a portion of said catalyst and a portion of said co-catalyst, and said process further comprises recovering and recycling said catalyst and said co-catalyst from said product stream.

19. The process of claim 18 wherein said catalyst and said co-catalyst are recovered and recycled as a mixture of the catalyst and co-catalyst.

20. The process of claim 12, wherein said haloalkane starting material comprises carbon tetrachloride.

21. The process of claim 12 wherein said catalyst comprises iron and said co-catalyst comprises tributlyphosphate.

* * * * *